(12) United States Patent
Damron

(10) Patent No.: US 7,080,420 B2
(45) Date of Patent: Jul. 25, 2006

(54) ADJUSTABLE HEAD-SUPPORT FOR THERAPY TABLES

(76) Inventor: Scott Damron, 3260 Lee St., Smyrna, GA (US) 30080

( * ) Notice: Subject to any disclaimer, the term of this patent is extended or adjusted under 35 U.S.C. 154(b) by 0 days.

(21) Appl. No.: 10/942,299

(22) Filed: Sep. 16, 2004

(65) Prior Publication Data

US 2006/0053557 A1    Mar. 16, 2006

(51) Int. Cl.
  *A47G 9/00*    (2006.01)
  *A61G 13/12*   (2006.01)
(52) U.S. Cl. .................. 5/640; 5/638; 5/641; 5/622; 5/643
(58) Field of Classification Search ............ 5/640, 5/638, 637, 641, 622, 636, 643
  See application file for complete search history.

(56) References Cited

U.S. PATENT DOCUMENTS

| | | | |
|---|---|---|---|
| 2,239,003 A | 4/1941 | Jones | |
| 2,461,434 A | 2/1949 | Moyers | |
| 2,688,142 A | 9/1954 | Jensen | |
| 3,289,224 A * | 12/1966 | Witchel | 5/703 |
| 3,315,282 A | 4/1967 | Lowery et al. | |
| 3,337,883 A * | 8/1967 | Allison | 5/638 |
| 4,504,050 A | 3/1985 | Osborne | |
| 4,531,247 A | 7/1985 | Eary, Sr. | |
| 5,165,137 A | 11/1992 | Amrein et al. | |
| 5,177,823 A | 1/1993 | Riach | |
| 5,214,815 A | 6/1993 | Agbodoe et al. | |
| 5,287,576 A | 2/1994 | Fraser | |
| 5,347,668 A * | 9/1994 | Manning | 5/622 |
| 5,427,436 A | 6/1995 | Lloyd | |
| 5,546,619 A | 8/1996 | Braun | |
| 5,613,501 A | 3/1997 | Michelson | |
| 5,615,432 A | 4/1997 | Von Ohlen, III | |
| 5,970,546 A | 10/1999 | Danis | |
| 6,023,801 A | 2/2000 | Lamm | |
| 6,049,926 A | 4/2000 | Amaral | |
| 6,273,865 B1 | 8/2001 | Perez | |
| 6,374,441 B1 | 4/2002 | Begell | |
| 6,397,414 B1 | 6/2002 | Lloyd | |
| 6,460,207 B1 * | 10/2002 | Papay et al. | 5/640 |
| 6,532,609 B1 | 3/2003 | Taylor et al. | |
| 6,658,681 B1 * | 12/2003 | Britto et al. | 5/655 |
| 2002/0096929 A1 | 7/2002 | Showerman | |
| 2002/0184706 A1 | 12/2002 | Riach | |
| 2003/0051293 A1 | 3/2003 | Chapman et al. | |
| 2004/0045087 A1 * | 3/2004 | Morris | 5/632 |
| 2004/0172064 A1 * | 9/2004 | MacDonald | 606/240 |

FOREIGN PATENT DOCUMENTS

| | | | |
|---|---|---|---|
| DE | 10038117 A1 | | 8/2001 |
| EP | 880925 A1 | | 12/1998 |
| GB | 638046 | * | 5/1950 |
| JP | 10117905 A | | 5/1988 |
| JP | 2000126016 A | | 5/2000 |
| JP | 2000139655 A | | 5/2000 |

* cited by examiner

*Primary Examiner*—Alexander Grosz
(74) *Attorney, Agent, or Firm*—Gregory Scott Smith; Christos S. Kyriakou

(57) ABSTRACT

A head rest that includes a cushion and a support plate. The facial surface area that contacts the cushion is maximized by using a contoured upper surface for the cushion, a contoured upper surface for the support plate or a combination of both. The head rest also includes a holder for aroma therapy items and a relief mechanism for the occipital nerves.

22 Claims, 6 Drawing Sheets

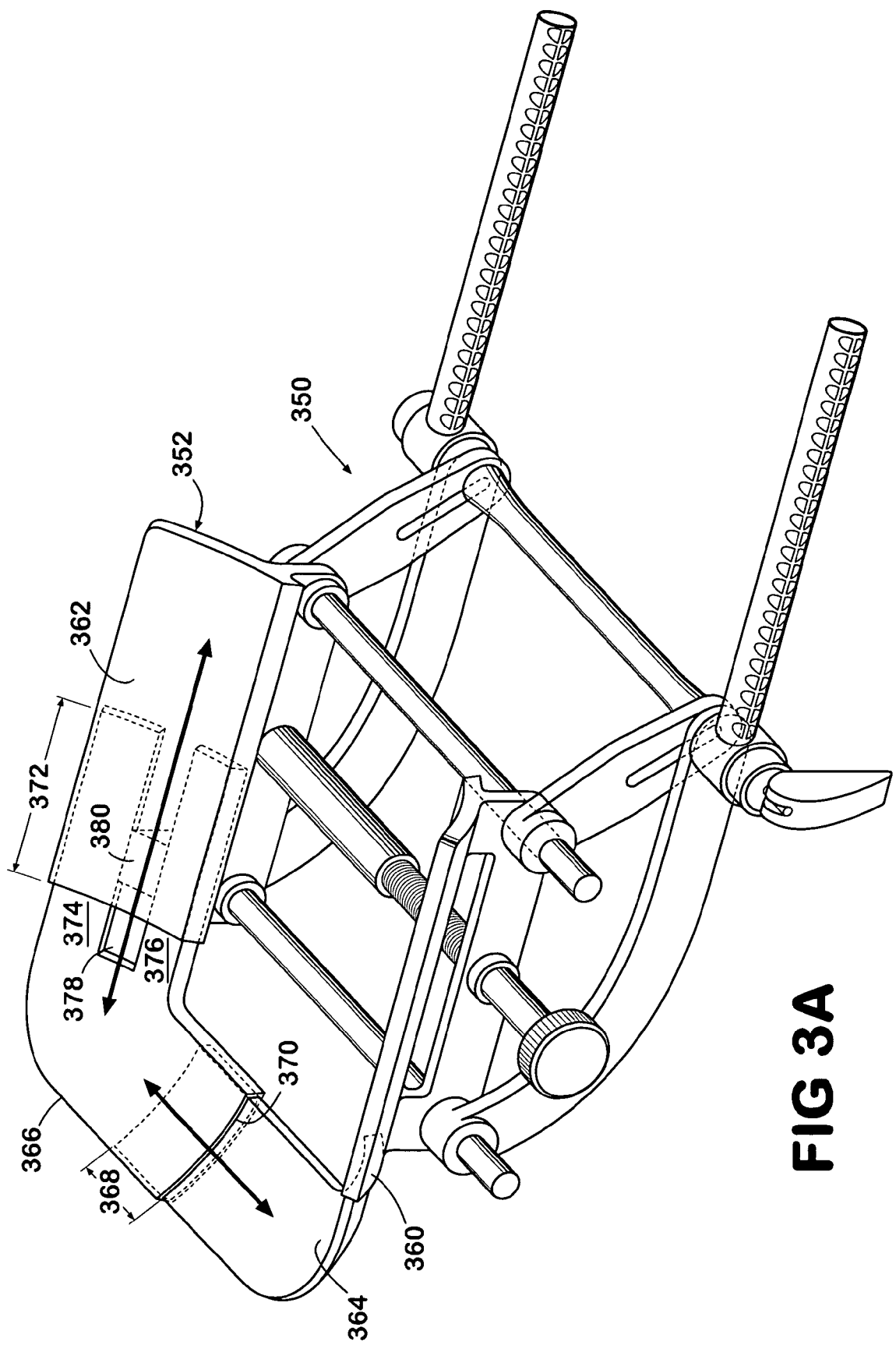

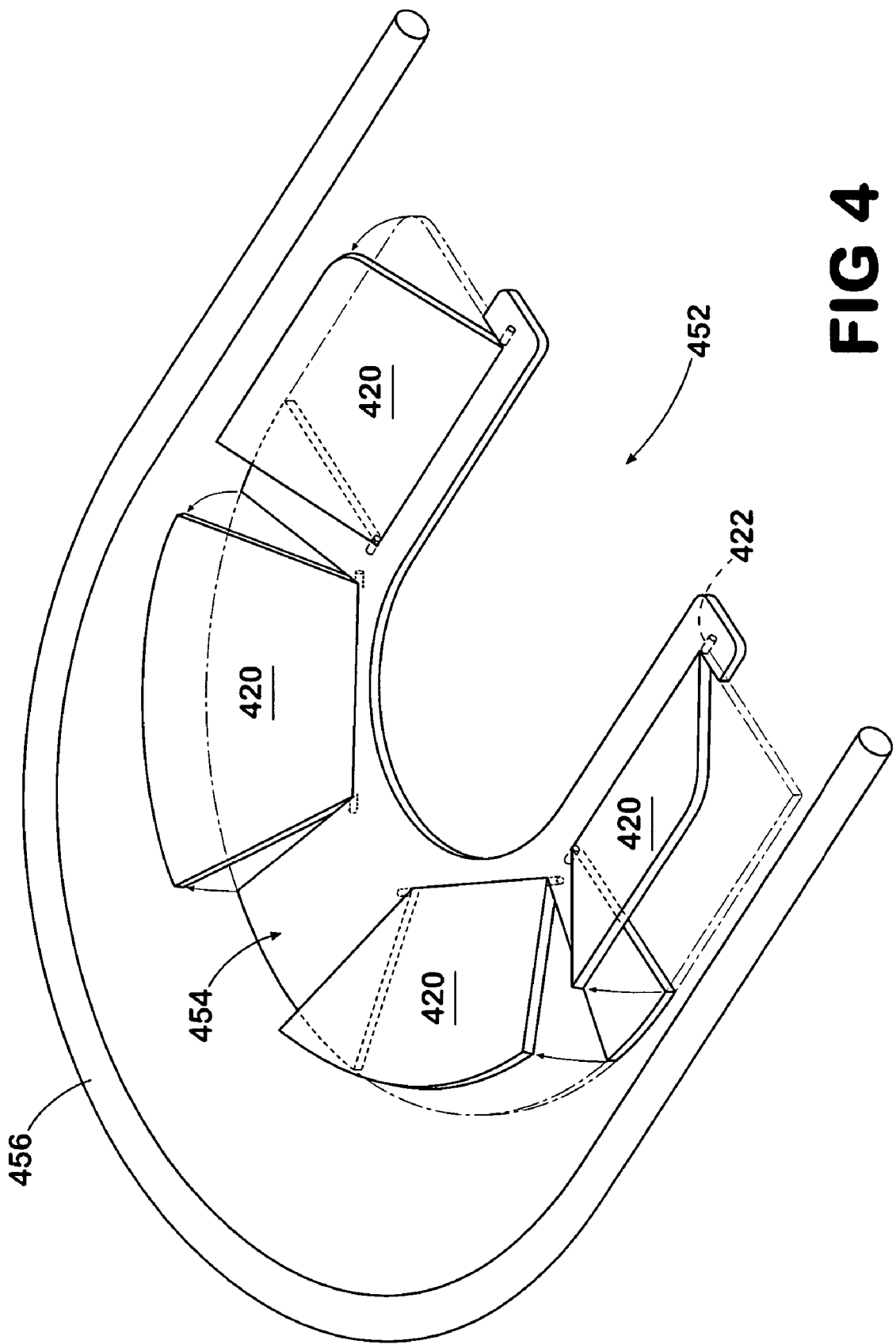

ADJUSTABLE HEAD-SUPPORT FOR THERAPY TABLES

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO SEQUENCE LISTING, A TABLE, OR A COMPUTER PROGRAM LISTING COMPACT DISK APPENDIX

Not applicable.

BACKGROUND OF THE INVENTION

The present invention is directed towards a supporting device for a therapy table and, more specifically, an adjustable head rest that can be easily adjusted for individual facial and head shapes to minimize unwanted pressure points when the patient is in the prone or supine positions.

Whether a patient is seeking a luxury massage or doctor recommended physical therapeutic massage, the main goal of the physical therapist or massage technician is the same— maximizing the comfort of the patient. Several advances have been made in the technology of the therapeutic and massage therapy equipment including portable tables, adjustable tables, the introduction of aroma therapy and the overall ambiance of the massage area. However, a technical issue that remains in the industry is maximizing the comfort of the patient without unduly hindering the ability of the therapist to perform his or her tasks with the patient.

One of the biggest technological hurdles is evident in the devices used to support the patient's head. When the patient is in the prone position, the main concern is the application of pressure on certain areas of the face. For example, pressure applied to the sinus areas of the face can create substantial discomfort to the patient by causing sinus drainage or inhibiting the patient's ability to clearly breathe. Identifying a solution to this problem is exasperated by the number of variances that exist in facial structures from one patient to the next. Thus, identifying an optimal configuration for a head rest that can be used for any patient is virtually an impossible task. One technique to address this problem is to utilize a set of head rests that are formed for various common facial structures. This technique is problematic in that it requires the therapist to select and match the appropriate head rest for the patient. In addition, for portable setups, the therapist is required to haul around the set of head rests. Thus, there is a need in the art for a head rest that is suitable for any facial structure and that minimizes unwanted pressure on various facial points.

BRIEF SUMMARY OF THE INVENTION

The present invention provides a solution to the above-mentioned needs in the art by providing a combined cushion and support structure that operates to distribute the pressure applied to the face of a subject in a more uniform manner over a wider surface area. Advantageously, this helps to alleviate undue pressure on sensitive areas such as the sinus areas and the ocular areas. Undue pressure in these areas can result in bringing discomfort to the subject and thus distract the subject from the enjoyment of a massage. This advantage of the present invention is provided in various embodiments. In one embodiment, a multi-surfaced contour is formed into a cushion. The contours allow the facial area that is supported by the cushion to be maximized. In other embodiment, a contoured support structure is used to deform a cushion that is placed on the support structure. The cushion is deformed in such a manner as to mold the surface of the cushion around the face of the subject, thereby increasing the facial area contacted. The contoured support structure can be a rigid contoured material, a rigid material with adjustable flaps, or a malleable material that a can be adjusted by applying force. In addition, a combination of a contoured cushion and a contoured support structure can be used to achieve these results.

The present invention also includes an aroma therapy element holder. This aspect of the invention incorporates a holder into the support structure for a cushion in such a manner that items of aroma therapy placed into the holder are held near the subjects face for enjoyment. In some embodiments, the position of the holder can be adjusted in accordance with the subject's preferences.

Another aspect of the present invention is an occipital relief mechanism. This aspect of the invention includes a flap that is pivotally hinged to the edge of the support structure. On one side of the flap, a finger like protrusion is included. When the flaps are moved into a closed position, the finger protrusions align with the occipital nerves of the subject and thus, when the subject is in a supine position, experiences the relief.

These and other aspects of the present invention are more fully described in conjunction with the figures, detailed description and the attached claims.

BRIEF DESCRIPTION OF THE SEVERAL VIEWS OF THE DRAWING

FIG. 3A is a perspective drawing of an embodiment of an adjustable support plate.

FIG. 4 illustrates a contour adjustment mechanism for a support plate.

DETAILED DESCRIPTION OF THE INVENTION

The present invention is directed towards an adjustable head-support that can be integrated into, or attached to a therapy table. One aspect of the present invention is to provide a head-support that minimizes patient discomfort due to excessive pressure being applied to more sensitive areas of the face. For instance, excessive pressure in the sinus region and cause significant discomfort to a patient. Another aspect of the invention is to provide an adjustable head rest that can easily conform to various facial structures. One method for providing this aspect of the present invention is through utilization of a formed cushion with a substantially rigid support plate. The formed cushion operates to maximize the distribution of the weight of the patient's head. The formed cushion is coupled with a substantially rigid plate that enables the shape of the cushion to be further altered individually for a patient. Another aspect of the present invention is to provide a mechanism to relieve pressure to the occipital nerve when the patient is in the supine position. Another aspect of the present invention is the introduction of an attachment to a headrest that can be used to hold aroma therapy oils or liquids in proximity to the patient's breathing passages.

Now turning to the figures in which like numerals and references refer to like elements throughout the several views, these aspects as well as other aspects of the present invention will be more fully described.

Figure 1:
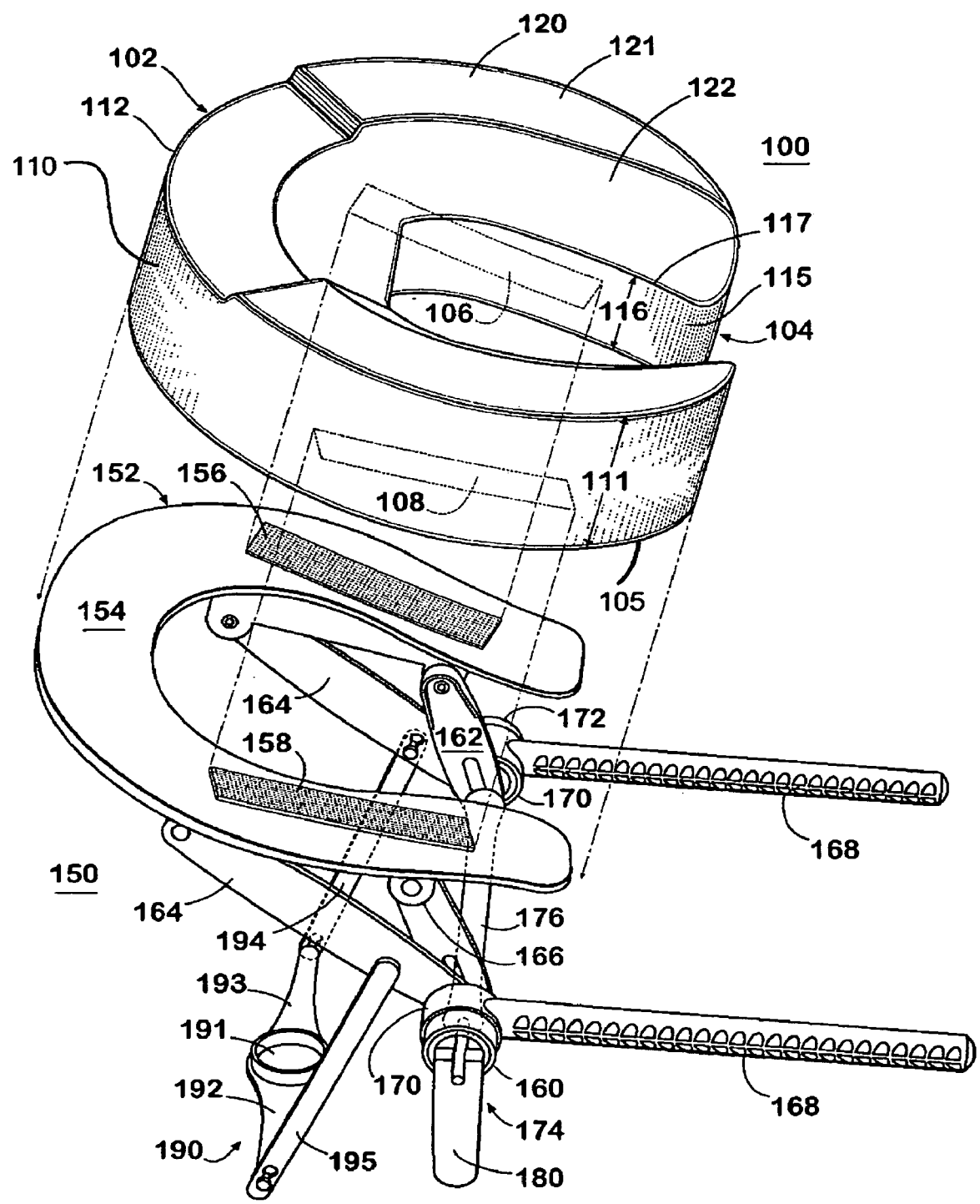
FIG. 1 is perspective drawing of a cushion and support structure for one embodiment of the present invention.

FIG. 1 is perspective drawing of a cushion and support structure for one embodiment of the present invention. FIG. 1 illustrates two main components, a contoured cushion 100 and a support structure 150. The cushion 100 is shown as having a generally U-shape structure however, other configurations are also anticipated including, but not limited to, a squared U or C shape structure, a V-shaped structure, an O-ring or open O-ring, or other similar type structures. Basically, the shape of the cushion 100 is such that it is operable to receive and hold the head of a patient, customer or user. Although the present invention is not limited to any particular structural shape of the cushion 100, the present invention will be described as being embodied within a substantially U-shaped structure.

The cushion 100 includes a closed end 102 and an open end 104. When the cushion 100 is used to receive a patient's head, the open end 104 is proximal to the patient's neck and chin where as the closed portion 102 is distal to the patient's neck and chin. The cushion 100 includes a bottom surface 105 that is substantially flat when the cushion is in an uncompressed state. It should be appreciated that the bottom surface 105 may also include ridges along the surface that can be used to help maintain the cushion 100 in position when placed on another surface. In addition, the cushion 100 may also include a series of protrusions that are fixedly attached to the cushion and extend below the bottom surface 105. The protrusions can be used to attach the cushion to a surface and thus, the protrusions may be threaded. Other techniques such as snaps, buckles or tie strings, as well as others may also be used to secure the cushion 100 to another surface and the present invention is not limited to any particular technique, although some of the listed techniques are considered novel. In the illustrated embodiment, the cushion 100 is shown as including two Velcro strips 106 and 108 that are mounted to the bottom surface 105.

The cushion 100 further includes an outer perimeter surface 110, an inner perimeter surface 115 and an upper surface 120. The outer perimeter surface 110 and the inner perimeter surface 115 are substantially parallel to each other and preferably, the inner height 116 of the inner perimeter surface 115 is less than the outer height 111 of the outer perimeter surface 110. The upper surface 120 is substantially flat proximate to the upper edge 112 of the outer perimeter surface 120 where the upper surface 120 adjoins the upper edge 112 of the outer perimeter surface 110. The upper surface 120 tapers down to the upper edge 117 of the inner perimeter surface 115. The taper of the upper surface 120 can consist of a flat portion 121 and a convex portion 122 as illustrated. However, the upper surface may also be substantially flat across the extension from the upper edge 112 of the outer perimeter surface 115 to the upper edge 117 of the inner perimeter surface 115, may be concave of the entire extension, may be convex over the entire extension or may include a combination of one or more of these configurations. Utilizing two or more of the identified tapers can advantageously maximize the facial contact of the upper surface 120 of the cushion 100. In addition, it will also be appreciated that similar advantages can be obtained by utilizing different foam densities in different areas of the cushion to help maximize the facial surface that is supported by the cushion.

FIG. 1 also illustrates a perspective diagram of a support structure 150 suitable for receiving the cushion 100. The support structure 150 includes a support plate on which the cushion 100 rests. The illustrated support plate 152 is a rigid or semi-rigid material and includes an upper surface 154 on which the bottom surface 105 of the cushion 100 can rest. Thus, the surface area of the upper surface 154 of the support plate 152 is substantially the same shape as the bottom surface 105 of the cushion 100. For the illustrated embodiment, the support plate 152 is substantially flat for receiving and supporting the bottom surface 105 of the cushion 100. In the embodiment of the cushion that includes ridges on the bottom surface, the upper surface of the support plate would include indentions aligned with the ridges of the bottom surface of the cushion. In the embodiment of the cushion that includes protrusions, the support plate would include holes that align with the protrusions from the bottom surface of the cushion. Similarly, the support plate may include matching buckles or tie downs for other various attachment mechanisms of the cushion. In the illustrated embodiment, the support plate 152 includes two Velcro strips 156 and 158 that mate with the Velcro strips 106 and 108 on the bottom surface 105 of the cushion 100 respectively.

The support plate 152 is shown as in a substantially U-shape configuration and is attached to a support rod 160 through a scissor-like support structure that includes a short upper leg 162 and a long lower leg 164. The scissor-like support structure is included on each leg of the U-shaped support plate 152. The support plate 152 includes two flanges 166 that depend from the bottom surface of the support plate 152 proximate to the legs. Because the structure used to connect the support plate 152 to the support rod 160 is mirrored for each leg of the support plate 152, only one side will be described. One end of short upper leg 160 is connected to the flange 166 on the support plate 152 and the support rod 160 passes through the other end of the short upper leg 162. Similarly, one end of the long lower leg 164 is connected to the flange 166 on the support plate 152 and the support rod 160 passes through the other end of the long lower leg 164.

Two attachment rods 168 are pivotally coupled to opposing ends of the support rod 166 by including a circular sleeve 170 through which the support rod 166 passes. The attachment rods 168 can he inserted and secured into a receiving slot or sleeve that is included in a therapy table (not shown). A stop 172 is attached to one end of the support rod 160 and retains the circular sleeve 170, the short upper leg 162 and the longer lower leg 164 on the support rod 160. A cam assembly is attached to the end of the support rod 160 opposite to the stop 172. An elongated and flanged sleeve 176 is located between the two sets of shorter upper arms 162, longer lower arms 164 and circular rings 172 and the support rod 160 extends through the elongated and flanged sleeve 176. When the cam lever 180 of the cam assembly 174 is moved to the open position (illustrated), the shorter upper legs 162, longer lower legs 174 and circular sleeves 170 can freely rotate around the support rod 166. When the cam lever 180 is placed into the closed position (not illustrated) the support rod 166 is pulled thereby forcing the stop 172 and the cam assembly 174 to force a friction onto the shorter upper legs 162, longer lower legs 174 and circular sleeves 170 there by preventing or restricting the ability to rotate or pivot. Advantageously, this structure allows the support plate 152 to be rotated coaxially to the axis of the support rod 166 and to adjust the plane of the support plate 152. It will be appreciated that although the support structure 150 may in and of itself include novel and non-obvious elements, other aspects of the present invention are not limited to utilization of the disclosed support structure 150 but rather, the disclosed support structure 150 is provided to illustrate a preferred embodiment of the various aspects of the present invention.

Another aspect of the present invention is an integrated holder for aroma therapy elements. FIG. 1 includes a perspective diagram illustrating a potion holder structure 190 for aroma therapy elements or potions. The potion holder structure 190 is adjustably or fixedly attached to the support structure 150.

The potion holder structure 190 can be attached to various locations on the support structure 150. For instance, the potion holder structure can be located approximately halfway between the closed end and the open end of the U-shaped support plate 152 and extend from the left side of the support plate 152 to the right side of the support plate 152.

The potion holder includes a cup, bowl or tray 191 that can hold various aroma therapy elements including oils, liquids, beads, flakes, herbs, potions or the like. Preferably the potion holder is adjustable so that the cup 191 can be placed in close proximity to the nose of the patient or retracted away from the patient's nose as desired.

In general, the illustrated embodiment shows an integrated holder that is suitably positioned in a manner to allow aroma from the aroma therapy elements to enter into the breathing intake area of a user resting their face the cushion 100 in a prone or kneeling position. In the illustrated embodiment, the cup 191 is integrally formed with two protruding arms 192 and 193. The protruding arms 192 and 193 are pivotally adjoined to adjustment swing arms 194 and 195 respectively. The adjustment swing arms 194 and 195 are then pivotally adjoined to the support structure 150. In the illustrated embodiment, the swing arms 194 and 195 are connected to the long lower leg 164; however, it will be appreciated that they could also be attached to the short upper leg 162 or to the support plate 152. In the various embodiments, the cup 191 hangs below the support plate 152, most preferably in front of a patient's face once the face is placed onto the cushion 100. In the adjustable embodiments, the patient can move the cup 191 to a position that provides a desired intensity of aroma. In other embodiments, the cup 191 may be fixedly attached to the support structure 150 so that the cup 191 maintains a constant position relative to the support structure 150.

Other configurations of the potion holder structure 190 are also anticipated, such as, a non-adjustable holder, a holder that only attaches to the support plate at one point, a malleable arm with a cup 191 located on the end, a telescoping arm or the like. The present invention anticipates various embodiments and the present invention should not be limited to any particular embodiment. The novel characteristic of this aspect of the present invention is the inclusion of a holder for aroma therapy potions in such a manner that the patient can enjoy aroma from a potion that is inserted into a holder that is integrated or attached to the head rest.

Figure 2:
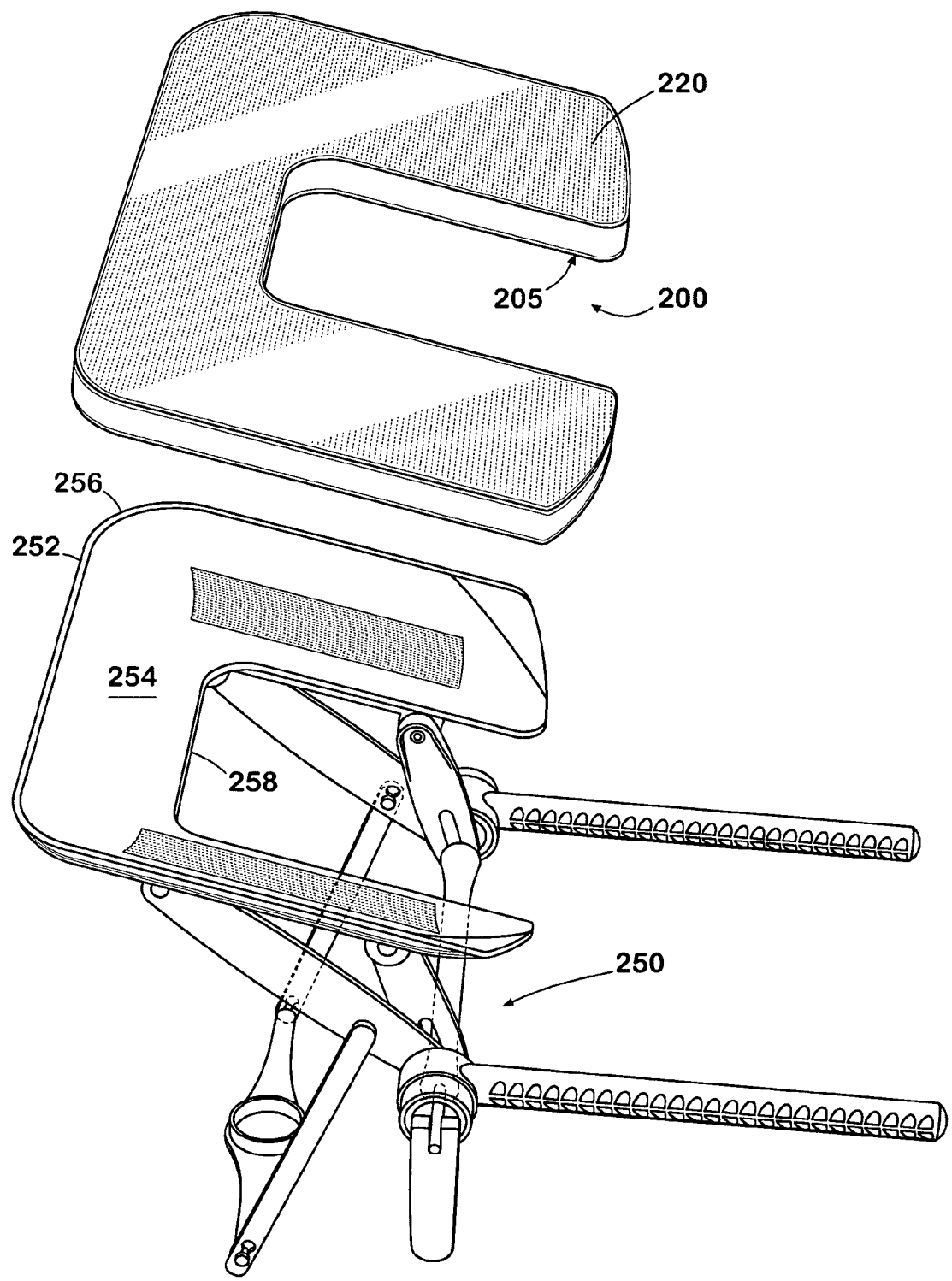
FIG. 2 is a perspective drawing illustrating another aspect of the present invention.

FIG. 2 is a perspective drawing illustrating another aspect of the present invention. The illustrated embodiment shows a cushion 200 and a support structure 250. The support structure 250 includes a support plate 252. The support plate 252 includes an upper surface 254 for receiving the bottom surface 205 of cushion 200. The upper surface 254 of support plate 252 is contoured. In the illustrated embodiment, the contour of the upper surface 254 is substantially convex. The upper surface includes an outer edge 256 and an inner edge 258. The outer edge 256 is higher than the inner edge 258. The convex surface of the upper surface 254 tapers down from the outer edge 256 to the inner edge 258. When the cushion 200 is placed onto the upper surface 254 of the support plate 252, the cushion 200 is compressed and deformed in accordance with the contour of the upper surface 254. Advantageously, this aspect of the present invention causes the cushion 200 to be deformed in a manner so that the upper surface 220 of the cushion 200 will come in contact with a larger area of a face being placed onto the upper surface 220 of the cushion 200 and thus, more effectively distribute the weight. This is accomplished because the upper surface of the cushion 200 is forced to be in closer proximity to the shape of a face.

It will be appreciated that although this aspect of the invention is illustrated as receiving a cushion 200 that has a substantially rectangular cross-section, the cushion presented in FIG. 1 and variations thereof can equally be utilized in this embodiment of the present invention. One of the advantages to this aspect of the present invention is that by utilizing a contoured support plate 252, a cushion can be forced into a shape that is more suitable for receiving a subject's face.

In addition, the upper surface 254 of the support plate 252 does not necessarily have to be convex. The upper surface can be flat and sloped, concave, or a combination of any two or more of these surface types.

Two embodiments of a support structure have been shown, support structure 150 in FIG. 1 and support structure 250 in FIG. 2. It will be appreciated that various aspects in each of these embodiments may also be incorporated into the other embodiment. FIG. 3A is a perspective drawing of an embodiment of an adjustable support plate. The support plate 352 is constructed of several components that can be used to adjust the length and width of the support plate 352. When the cushion is attached to the support plate 352, the adjustments to the support plate 352 result in a compression or expansion of the cushion, thereby allowing the cushion to be formed to various facial structures.

More specifically, the illustrated support plate 352 includes four components: a left-chin proximal plate 360, a right-chin proximal plate 362, a left-forehead proximal plate 364 and a right-forehead proximal plate 366. The interconnected plates can be attached to each other using a variety of techniques that are well known in the art and will be readily apparent. For purposes of understanding the operation of the invention, a particular embodiment is being illustrated. The components of the support plate 353 are slideably connected to each other. At the joints of the various plates, one plate has a slightly smaller width than the other plate. The wider plate may include an integral sleeve that receives the narrower plate or may be hollow, thereby receiving the narrow portion of the plate. For instance, the left-forehead proximal plate 364 has a small width than the right-forehead proximal plate 366. At the joint 368 between the left-forehead proximal plate 364 and the right-forehead proximal plate 366, the left-forehead proximal plate 364 slides into a hollow opening 370 in the right-forehead proximal plate 366.

The joint 372 between the right-chin proximal plate 362 and the right-forehead proximal plate 366 is illustrated using another potential configuration. In this embodiment, a tongue and groove type structure is illustrated. The right finger 374 and the left finger 376 form a groove 378 in the right-forehead proximal plate 366. The groove 378 slideably engages a tongue 380 integrated into the right-chin proximal plate 362. In this illustrated embodiment, the right-forehead proximal plate 366 slides along the lower surface of the right-chin proximal plate 362 rather than being inserted through a hollow opening in the right-chin proximal plate 362.

It should be appreciated that the sliding engagements for joint 368 and joint 372 are simply two illustrations of how the present invention can be implemented and are not intended to limit the present invention to any particular structure. Rather, this inventive aspect of the present invention includes the ability to adjust the width and the length of the support plate 352 and thereby, allow the support plate to compress or expand an attached cushion to conform to various facial structures.

Figure 3B:
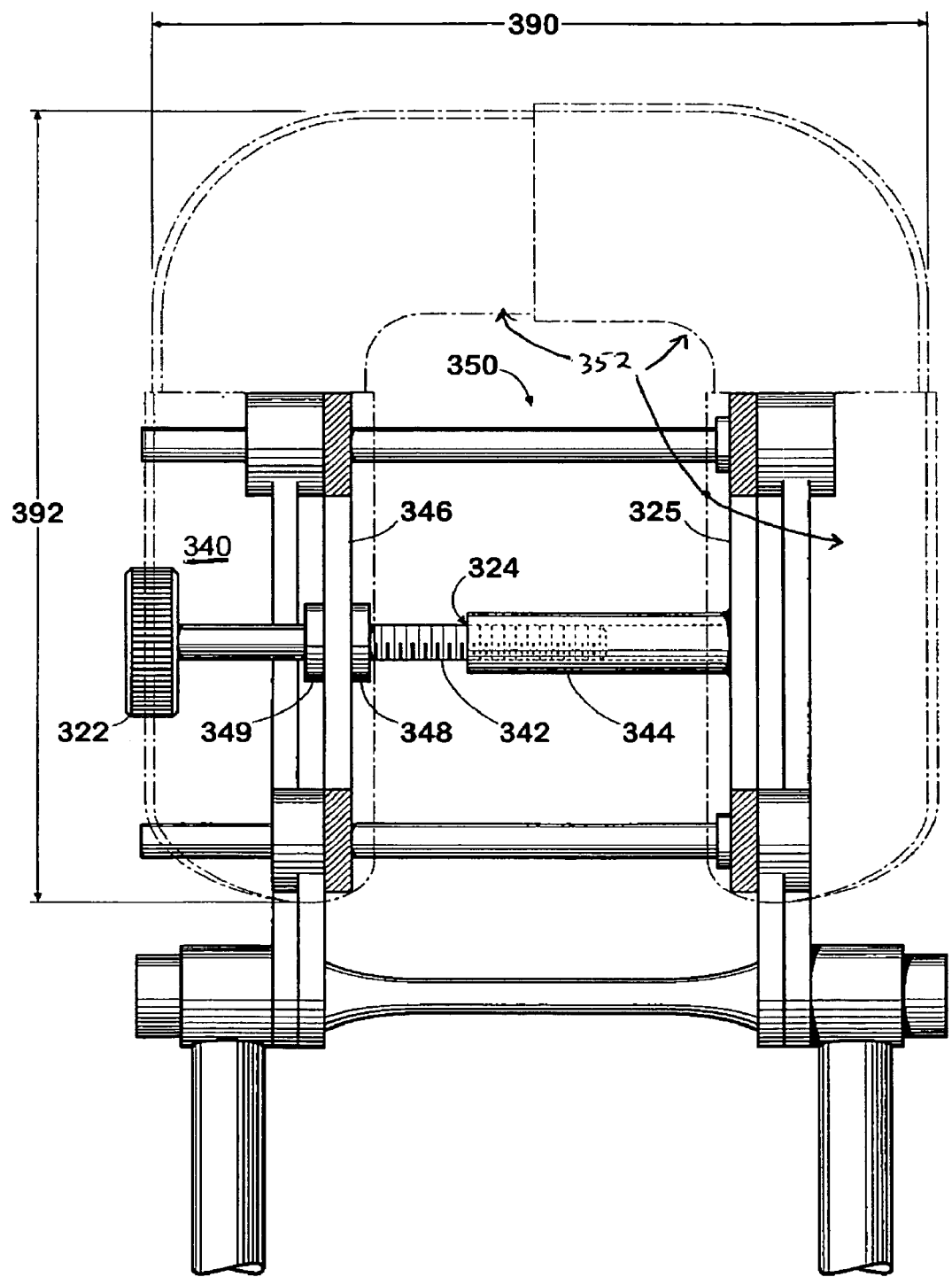
FIG. 3B is a bottom view of the support structure illustrated in FIG. 3A.

FIG. 3B is a bottom view of the support structure illustrated in FIG. 3A. Referring to FIGS. 3A–3B a mechanism for actuating the adjustment of the support plate 352 is illustrated. The width 390 of the support plate 352 is adjusted by actuating an adjustment assembly 340. The illustrated adjustment assembly includes a threaded shaft 342 and a threaded sleeve 344. The threaded shaft 342 extends through flange 346, which is fixedly attached to the bottom surface of right-chin proximal plate 366. Two washer-like flanges are attached to the threaded shaft 342, an inner washer 348 exists near the inside surface of the flange 346 and the outer washer 349 exists near the outside surface of the flange 346. A knob 322 is integrally formed or fixedly attached to an unthreaded end of threaded shaft 342. The threaded shaft 342 extends through the flange 346 in such a manner the threaded screw 342 is free to turn in response to rotating the knob 352.

The threaded portion of threaded shaft 342 is inserted into the opening 324 of threaded sleeve 344. The threaded sleeve 344 is fixedly coupled to a flange 325, which is fixedly attached to the bottom surface of the left-chin proximal plate 360. When the adjustment knob 322 is turned in one direction, the threaded screw 342 penetrates into the threaded sleeve 344. The outer washer 349 engages the outside surface of the flange 346 thereby encouraging the right-forehead proximal plate 366 to move towards the left-forehead proximal plate 364 thereby decreasing the width 390 of the support plate 352. When the adjustment knob 322 is turned in the opposite direction, the threaded screw 342 backs out of the threaded sleeve 344. During this process, the inner washer 348 engages the inside surface of the flange 346 thereby encouraging the right-forehead proximal plate 366 to move away from the left-forehead proximal plate 364 and thus, increasing the width 390 of the support plate 352. Again, it will be appreciated that the illustrated embodiment is not limiting on the present invention but is simply provided for illustrative purposes. Alternate embodiments include, but are not limited to, (a) providing serrated edges that allow the plates to be slid in and out with force but will be held in place at the absence of such force (b) providing a clamping lever to secure the various plates into position, (c) providing tightening wing nut screws to secure the plates in position.

In addition, it will be appreciated that although the supporting plate 352 includes both width 390 and length 392 adjustments, other embodiments may only include one of the two available adjustments. Thus, it can be appreciated that the embodiment illustrated in FIGS. 3A–B allow the support structure 350 to adjust the width 390 and the length 392 of the support plate 352. When a cushion, such as cushion 100 or cushion 200 is attached to the support plate 352, the cushion will be either compressed or stretched in conformance with the adjustments to the support plate 352. In an embodiment that only allows for the adjustment of the width, the support plate will include at least two interconnected plates: a left plate and a right plate. As previously described, the interconnected plates can be attached to each other using a variety of techniques but in the preferred embodiment, the plates are slideably connected to each other. At the joints of the left plate and the right plate, near the apex of the U-shape, one plate has a slightly smaller width than the other plate. The wider plate may include an integral sleeve or bowed flanges that receive the narrower plate. The bowed flanges are attached to the edges of a common surface of the receiving plate and are configured in such a manner to receive the end portion of the sliding plate. It should be appreciated that multiple sets of the bowed flanges can be utilized to provide additional structural support and the receiving plate can be either the left plate or the right plate. The ends of the sliding plate may include a stop to prevent the sliding plate from being fully retracted from the bowed flanges of the receiving plate.

FIG. 4 illustrates a contour adjustment mechanism for a support plate. The support plate 452 includes one or more adjusting flaps 420 that can be used to adjust the contour of the support plate 452. Each of the adjusting flaps 420 are hinged to the main body 422 of the support plate 452 in a restrictive manner that allows a force applied to the adjustable flap 420 to cause the adjustable flap 420 to move away from the force and when the force is released, to maintain the new position, even in the presence of a slight force. Thus, the adjusting flaps 420 can be used to alter the overall shape of the upper surface 454 of the support plate 452. Similar to the embodiment illustrated in FIG. 2 with a contoured support plate 252, the support plate 452 alters the configuration of a cushion that is placed onto the upper surface 454 of the support plate 452. For instance, if the flaps 420 are raised, a cushion placed on the upper surface 454 will be compressed so that the inner portion of the cushion will be drawn down and away from the face and the upper portion of the cushion will be drawn up towards the face. This action results in creating more contact between the subjects face and the cushion. This compression of the cushion results in modifying the contour of the upper surface of the cushion. Advantageously, this aspect of the present invention allows the upper surface of the cushion to be adjusted for various facial structures. The flaps 420 can be set to a variety of settings thereby providing great flexibility in the adjustment of the cushion. Alternatively, a piping 456 can be used as to secure the flaps 420 to a desired setting.

In an alternate embodiment of the present invention, the support plate can be constructed of a malleable material that can be deformed by the application of a force but that is rigid enough to maintain its shape under normal operating conditions (i.e., in supporting a patient's head). Such a material can include various aluminum alloys or lead based metals as are commonly found in medical devices such as removable casts and splints. Advantageously, this embodiment of the invention allows the support plate to be adjusted in a variety of manners. Each of the adjustments to the support plate equate with compressions or expansions of the cushion attached to the support plate. Thus, the upper surface of the cushion can be infinitely adjusted to fit the contours of any facial structure.

Figure 5:
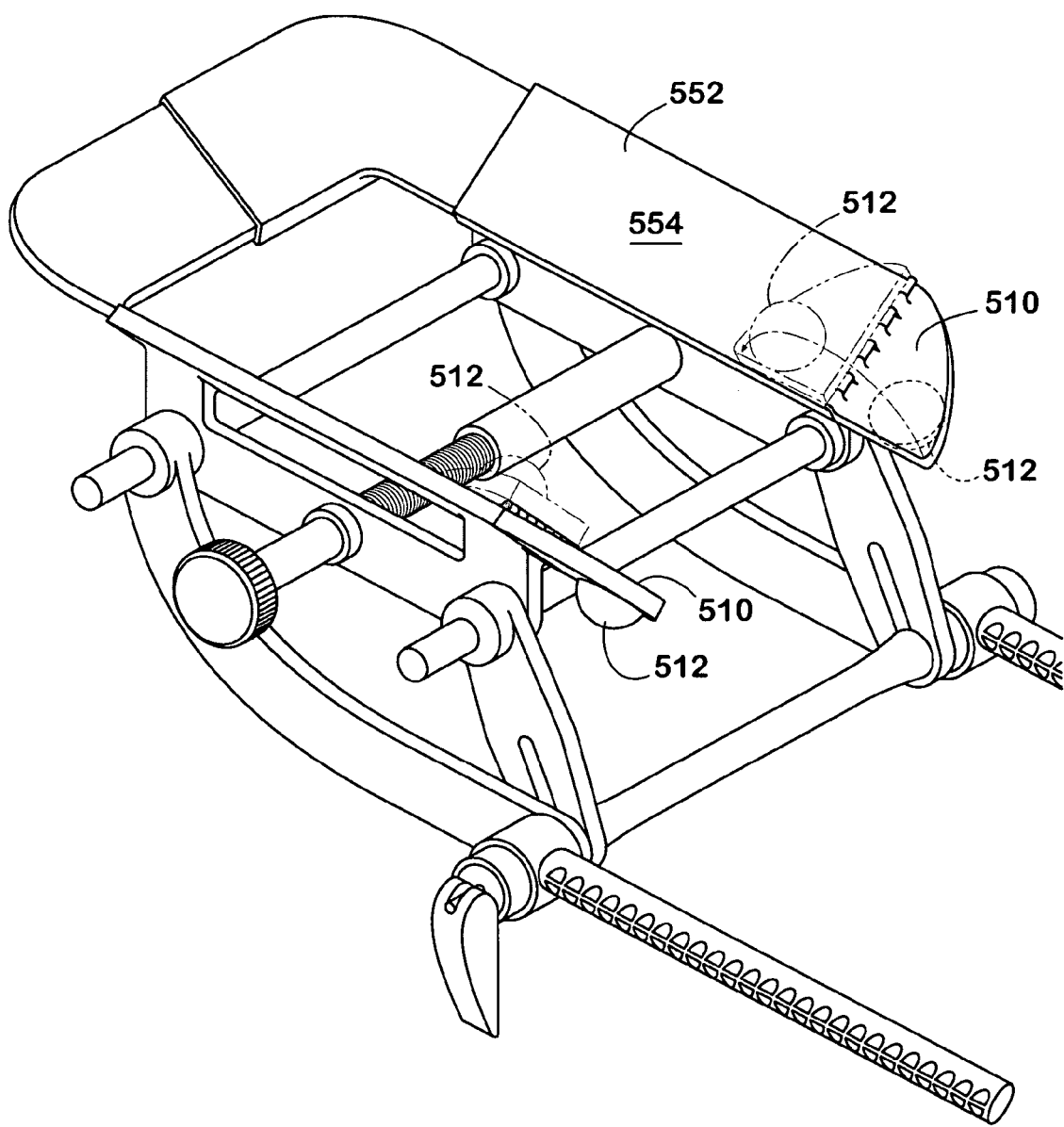
FIG. 5 is a perspective diagram illustrating an occipital relief aspect of the present invention.

FIG. 5 is a perspective diagram illustrating an occipital relief aspect of the present invention. When the subject is in the supine position, significant pressure can be imposed on the occipital nerve which is located near the base of the skull. The present invention utilizes a finger protrusion that is attached to the support plate and operates to relieve pressure to the occipital nerve. On proximal ends of the legs of the U-shape support plate 552, a flap 510 is pivotally attached to the edge of the support plate 552. One side of the flap 510 includes a finger protrusion 512. When the flap 510 is moved to the closed position, the finger protrusion 512 extends up from the surface 554 of the support plate 552. When the flap is in the open position, the finger protrusion 512 is moved out of the way. When the subject is in a prone position, the finger protrusions are pivoted into the open position so that they are below the upper surface of the support plate and thus, do not interfere with the patient when the patient places his or her face on the cushion. However, when the patient moves into a supine position, the finger protrusions are pivoted into the closed position so that the finger protrusion 512 extends vertically from the upper surface 554 of the support plate 552 and can engage the occipital nerve of the patient. Various embodiments of this aspect of the present invention are anticipated and include, but are not limited to, a finger protrusion that can be slid onto the support plate 552, a finger protrusion that can be snapped onto the support plate 552, a support plate overlay that can be laid over the top of the support plate 552, the overlay including integrally formed finger protrusions. In addition, rather than having two flaps or two separate pieces, the finger protrusion for each side of the support plate can be integrated into a single flap or unit. Other embodiments of this aspect of the present invention are also anticipated and the disclosed embodiments are not intended to limit this aspect of the present invention in any manner.

The present invention has been described using detailed descriptions of embodiments thereof that are provided by way of example and are not intended to limit the scope of the invention. The present invention can be implemented as a process that runs within a variety of system environments or as an entire system including various components. The described embodiments comprise different features, not all of which are required in all embodiments of the invention. Some embodiments of the present invention utilize only some of the features, aspects or possible combinations of the features or aspects. Variations of embodiments of the present invention that are described and embodiments of the present invention comprising different combinations of features noted in the described embodiments will occur to persons of the art.

What is claimed is:

1. An apparatus for supporting a subject's head, the apparatus comprising:
   a cushion;
   a support structure including a rigid support plate for receiving the bottom surface of the cushion;
   the support plate being contoured and thus, deforming the cushion when the cushion is placed onto the support plate,
   wherein the support plate includes at least a front plate and two back plates, the front plate and the two back plates slideably adjoining, and the length of the support plate is adjusted by sliding the front plate towards the two back plates or pulling the front plate away from the two back plates.

2. The apparatus of claim 1, wherein the support plate includes:
   an outer edge;
   an inner edge;
   an upper surface; and
   the support plate is contoured by the outer edge being elevated and the upper surface extending down to the inner edge.

3. The apparatus of claim 2, wherein the upper surface is convex.

4. The apparatus of claim 2, wherein the upper surface is flat.

5. The apparatus of claim 2, wherein the upper surface is concave.

6. The apparatus of claim 2, wherein portions of the upper surface include two of the surface types selected from the group of: flat, concave and convex.

7. The apparatus of claim 1, wherein the support plate includes at least a left plate and a right plate, the left plate and right plate slideably adjoining at a joint, and the width of the support plate is adjusted by sliding the right plate and left plate towards each other or pulling the right plate and the left plate away from each other.

8. The apparatus of claim 1, further comprising a bowl that is held below the support plate and is operable to receive aroma therapy elements.

9. The apparatus of claim 8, wherein the location of the bowl relative to the support structure can be adjusted.

10. The apparatus of claim 1, wherein the rigid support plate is malleable by application of force.

11. The apparatus of claim 1, wherein the support plate is substantially U-shaped having a first and a second leg, further comprising:
    a first flap pivotally connected to the end of the first leg;
    a second flap pivotally connected to the end of the second leg;
    a finger protrusion on the back side of the first and second flaps;
    the first and second flaps being pivotal between an open and closed position and, when in the closed position, the finger protrusions are in approximate relation to the occipital nerve of a subjects head when the subject is in the supine position.

12. The apparatus of claim 11, further comprising a bowl that is held below the support plate and is operable to receive aroma therapy elements.

13. The apparatus of claim 12, wherein the location of the bowl relative to the support structure can be adjusted.

14. The apparatus of claim 11, wherein the rigid support plate is malleable by application of force.

15. The apparatus of claim 11, wherein the support plate is substantially U-shaped having a first and a second leg, further comprising:
    a first flap pivotally connected to the end of the first leg;
    a second flap pivotally connected to the end of the second leg;
    a finger protrusion on the back side of the first and second flaps;
    the first and second flaps being pivotal between an open and closed position and, when in the closed position, the finger protrusions are in approximate relation to the occipital nerve of a subjects head when the subject is in the supine position.

16. An apparatus for supporting a subject's head, the apparatus comprising:
    a cushion;
    a support structure including a rigid support plate for receiving the bottom surface of the cushion;
    the support plate being contoured and thus, deforming the cushion when the cushion is placed onto the support plate, wherein the support plate includes a plurality of plates that are slideably adjoined, and the length and the width of the support plate can be adjusted by sliding one or more of the plurality of plates.

17. The apparatus of claim 16, wherein the support plate includes:
 an outer edge;
 an inner edge;
 an upper surface; and
 the support plate is contoured by the outer edge being elevated and the upper surface extending down to the inner edge.

18. The apparatus of claim 17, wherein the upper surface is convex.

19. The apparatus of claim 17, wherein the upper surface is flat.

20. The apparatus of claim 17, wherein the upper surface is concave.

21. The apparatus of claim 17, wherein portions of the upper surface include two of the surface types selected from the group of: flat, concave and convex.

22. The apparatus of claim 16, wherein the support plate includes at least a left plate and a right plate, the left plate and right plate slideably adjoining at a joint, and the width of the support plate is adjusted by sliding the right plate and left plate towards each other or pulling the right plate and the left plate away from each other.

* * * * *